United States Patent [19]

Keller et al.

[11] Patent Number: 4,578,401

[45] Date of Patent: Mar. 25, 1986

[54] MENTAL COMPLEXES HAVING AN ANTINEOPLASTIC ACTION, AND MEDICAMENTS CONTAINING THESE COMPLEXES

[75] Inventors: Heimo Keller; Bernhard Keppler, both of Heidelberg; Uwe Krüger; Rudolf Linder, both of Constance, all of Fed. Rep. of Germany

[73] Assignee: Byk Gulden Lomberg Chemische Fabrik GmbH, Constance, Fed. Rep. of Germany

[21] Appl. No.: 491,337

[22] PCT Filed: Aug. 28, 1982

[86] PCT No.: PCT/EP82/00184

§ 371 Date: Apr. 29, 1983

§ 102(e) Date: Apr. 29, 1983

[87] PCT Pub. No.: WO83/00868

PCT Pub. Date: Mar. 17, 1983

[30] Foreign Application Priority Data

Sep. 2, 1981 [DE] Fed. Rep. of Germany .....................

[51] Int. Cl.⁴ .................. A01N 55/04; C07F 7/00; C07F 7/28; A61K 31/32
[52] U.S. Cl. .................................. 514/49; 556/40
[58] Field of Search ............. 260/429.5, 429.3, 429 R; 424/287

[56] References Cited

U.S. PATENT DOCUMENTS 3,334,067  8/1967  Weyenberg ................. 260/46.5

FOREIGN PATENT DOCUMENTS 2079013  11/1971  France .
2121289  8/1972  France .

1473335  5/1977  United Kingdom .

OTHER PUBLICATIONS

Puri, Chemical Abstracts, vol. 58, No. 4, 3343h, 2/18/63.
Saxena, J. Chem. Soc. (A), 904–907, 1970.
Yamamoto, J.A.C.S., vol. 79, 4344–4348, 8/20/57.

*Primary Examiner*—Helen M. S. Sneed
*Attorney, Agent, or Firm*—Berman, Aisenberg & Platt

[57] ABSTRACT

Metal complexes of the general formula I

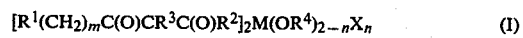

$$[R^1(CH_2)_m C(O)CR^3 C(O)R^2]_2 M(OR^4)_{2-n} X_n \qquad (I)$$

wherein M denotes titanium, zirconium or hafnium, $R^1$ denotes hydrogen, $C_1$–$C_8$-alkyl or phenyl, which can be monosubstituted or polysubstituted by fluorine, chlorine, bromine, nitro, $C_1$–$C_4$-alkyl, $C_1$–$C_4$-alkoxy or trifluoromethyl, $R^2$ denotes $C_1$–$C_8$-alkyl, or phenyl, which can be monosubstituted or polysubstituted by fluorine, chlorine, bromine, nitro, $C_1$–$C_4$-alkyl, $C_1$–$C_4$-alkoxy or trifluoromethyl, $R^3$ denotes hydrogen or phenyl, $R^4$ denotes $C_1$–$C_{18}$-alkyl, which can be substituted by hydroxyl, $C_1$–$C_3$-alkylamino or alkali metal sulfonato groups, or denotes $C_5$–$C_8$-cycloalkyl, which can be substituted by $C_1$–$C_5$-alkyl groups, hydroxyl or alkali metal sulfonato groups, X denotes fluorine, chlorine or bromine, m denotes the number 0 or 1, but does not denote 0 if $R^1$ denotes hydrogen, and n denotes the number 0 or 1, and, if a radical $R^4$ contains an amino group, hydrohalides thereof, exhibit a very good cytostatic activity, coupled with low toxicity. They are suitable for the production of medicaments having an antineoplastic action.

20 Claims, No Drawings

MENTAL COMPLEXES HAVING AN ANTINEOPLASTIC ACTION, AND MEDICAMENTS CONTAINING THESE COMPLEXES

TECHNICAL FIELD

The invention relates to metal complexes having an antineoplastic action and to medicaments containing these complexes.

PRIOR ART

A medicament which contains the complex compound cis-diamminodichloroplatinum(II) has recently been marketed as a chemotherapeutic agent against cancer. This compound, known by the International Nonproprietary Name (INN) of cisplatin has proved to be an extremely potent antitumoral agent, especially in the treatment of testicular tumors, and also, for example, of ovarian tumors and parvicellular bronchial carcinomas. The disadvantage of cisplatin is its relatively high toxicity. Its nephrotoxicity and its action leading to lasting damage to hearing are particularly serious. Renal damage and damage to hearing are found with considerable frequency after administration of only a single therapeutic dose. Besides the nephrotoxic and haematoxic action, the long-lasting severe nausea and the retching associated therewith are, above all, also extremely unpleasant for the patients.

Numerous other platinum complexes (German Offenlegungsschrift No. 2,445,418, German Offenlegungsschrift No. 2,837,237, German Offenlegungsschrift No. 2,626,559 and German Offenlegungsschrift No. 2,539,179) and complex compounds of other transition metals have recently been proposed as agents having a cytostatic action. In German Offenlegungsschrift No. 2,801,355, a brown amorphous complex which is obtained by reacting ascorbic acid with a titanium(III) compound and a copper (II) compound (in a molar ratio of 36:1:6) is said to have curative and prophylactic actions against, inter alia, leukemia. It has been reported that titanocene dichloride, zirconocene dichloride and hafnocene dichloride have an inhibiting action on ascitic Ehrlich tumors in mice [P.Köpf-Maier, B. Hesse and H. Köpf, J. Cancer Res. Clin. Oncol. 96, 43 (1980)]. Dihalogenobis-(1,3-diketonato)-tin, -titanium, -zirconium and -hafnium compounds having an antineoplastic activity are described in European Laid-Open Application 49,486.

DESCRIPTION OF THE INVENTION

Surprisingly, it has now been found that the metal complexes of the general formula I $$[R^1(CH_2)_mC(O)CR^3C(O)R^2]_2M(OR^4)_{2-n}X_n \qquad (I)$$

wherein

M denotes titanium, zirconium or hafnium, $R^1$ denotes hydrogen, $C_1$–$C_8$-alkyl or phenyl, which can be monosubstituted or polysubstituted by fluorine, chlorine, bromine, nitro, $C_1$–$C_4$-alkyl, $C_1$–$C_4$-alkoxy or trifluoromethyl, $R^2$ denotes $C_1$–$C_8$-alkyl, or phenyl, which can be monosubstituted or polysubstituted by fluorine, chlorine, bromine, nitro, $C_1$–$C_4$-alkyl, $C_1$–$C_4$-alkoxy or trifluoromethyl, $R^3$ denotes hydrogen or phenyl, $R^4$ denotes $C_1$–$C_{18}$-alkyl, which can be substituted by hydroxyl, $C_1$–$C_3$-alkylamino or alkali metal sulfonato groups, or denotes $C_5$–$C_8$-cycloalkyl, which can be substituted by $C_1$–$C_5$-alkyl groups, hydroxyl or alkali metal sulfonato groups, X denotes fluorine, chlorine or bromine, m denotes the number 0 or 1, but does not denote 0 if $R^1$ denotes hydrogen, and n denotes the number 0 or 1, and, if a radical $R^4$ contains an amino group, hydrohalides thereof, have an interesting cytostatic activity coupled with an advantageous therapeutic range, and are suitable as chemotherapeutic agents for the treatment of cancers. They are useful as chemotherapeutic agents with few side effects for the treatment of tumors, e.g. ovarian tumors, testicular tumors, carcinomas of the prostate, bronchial carcinomas, carcinomas of the urinary bladder, oesophagal carcinomas and other malignant neoplasias. Accordingly, the compounds are useful for alleviation of pain and suffering in connection with cancer therapy, remission, alleviation of symptoms and extension of life expectancy.

The invention thus relates to medicaments containing one or more metal complexes of the above general formula I, wherein M, $R^1$, $R^2$, $R^3$, $R^4$, X, m and n have the abovementioned meanings, in particular for combating cancers.

Medicaments containing one or more metal complexes of the general formula I'

$$[R^{1'}(CH_2)_{m'}C(O)CR^{3'}C(O)R^{2'}]_2M'(OR^{4'})_{2-n}X'_n \qquad (I')$$

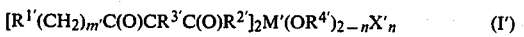

wherein

M' denotes titanium, zirconium or hafnium, $R^{1'}$ denotes hydrogen, $C_1$–$C_6$-alkyl, or phenyl, which can be monosubstituted or polysubstituted by fluorine, chlorine, bromine, nitro, $C_1$–$C_2$-alkyl, $C_1$–$C_2$-alkoxy or trifluoromethyl, $R^{2'}$ denotes $C_1$–$C_6$-alkyl or phenyl, which can be substituted by $C_1$–$C_2$-alkoxy, $R^{3'}$ denotes hydrogen or phenyl, $R^{4'}$ denotes $C_2$–$C_{16}$-alkyl, which can be substituted by hydroxyl, $C_1$–$C_3$-alkylamino or alkali metal sulfonato groups, or denotes cyclohexyl, which can be substituted by $C_1$–$C_4$-alkyl groups, X' denotes fluorine or chlorine, m' denotes the number 0 or 1, but does not denote 0 if $R^{1'}$ denotes hydrogen, and n denotes the number 0 or 1, and, if a radical $R^{4'}$ contains an amino group, hydrohalides thereof, are particularly preferred.

Medicaments containing one or more metal complexes of the general formula I"

$$[R^{1''}(CH_2)_{m''}C(O)CR^{3''}C(O)R^{2''}]_2M''(OR^{4''})_{2-n}X''_n \qquad (I'')$$

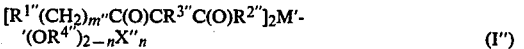

wherein

M" denotes titanium, zirconium or hafnium, $R^{1''}$ denotes hydrogen, $C_1$–$C_4$-alkyl or phenyl, which can be substituted by $C_1$–$C_2$-alkoxy, $R^{2''}$ denotes $C_1$–$C_4$-alkyl or phenyl, $R^{3''}$ denotes hydrogen or phenyl, $R^{4''}$ denotes $C_2$–$C_{13}$-alkyl, which can be substituted by a hydroxyl, a di-$C_1$–$C_3$-alkylamino or an alkali metal sulfonato group, or denotes 1-isopropyl-4-methylcyclohex-2-yl, X" denotes chlorine, m″ denotes the number 1, if R¹″ denotes hydrogen, or the number 0, if R¹″ denotes phenyl, and n denotes the number 0 or 1, and, if a radical R⁴″ contains an amino radical, hydrochlorides thereof, are particularly preferred.

Medicaments containing compounds of the above formulae I, I′ and I″ wherein the variables R¹, R¹′ and R¹″, R², R²′ and R²″, R³, R³′ and R³″, R⁴, R⁴′ and R⁴″, X, X′ and X″, m, m′ and m″ and n have the abovementioned meanings, but M, M′ and M″ in each case denote only titanium, form particular embodiments of the invention.

Medicaments containing diethoxybis-(1-phenyl-1,3-butanedionato)-titanium(IV), diisopropoxy-bis-(1-phenyl-1,3-butanedionato)-titanium(IV), bis-(2-hydroxypropoxy)-bis-(1-phenyl-1,3-butanedionato)-titanium(IV) and/or diethoxybis-(3-phenyl-2,4-pentanedionato)-titanium(IV), are particularly preferred.

The invention also relates to the use of the compounds of the general formulae I, I′ and I″ for combating cancers and for the production of medicaments, especially medicaments against cancers.

The compounds of the general formula I$^a$

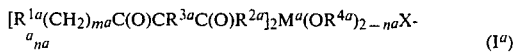

$$[R^{1a}(CH_2)_{m^a}C(O)CR^{3a}C(O)R^{2a}]_2 M^a(OR^{4a})_{2-n^a}X^a_{n^a} \qquad (I^a)$$

wherein

M$^a$ denotes titanium, zirconium or hafnium,

R$^{1a}$ denotes hydrogen, C$_1$-C$_8$-alkyl, or phenyl, which can be monosubstituted or polysubstituted by fluorine, chlorine, bromine, nitro, C$_1$-C$_4$-alkyl, C$_1$-C$_4$-alkoxy or trifluoromethyl, R$^{2a}$ denotes C$_1$-C$_8$-alkyl, or phenyl, which can be monosubstituted or polysubstituted by fluorine, chlorine, bromine, nitro, C$_1$-C$_4$-alkyl, C$_1$-C$_4$-alkoxy or trifluoromethyl, R$^{3a}$ denotes hydrogen or phenyl, R$^{4a}$ denotes C$_1$-C$_{18}$-alkyl, which can be substituted by hydroxyl, C$_1$-C$_3$-alkylamino or alkali metal sulfonato groups, or denotes C$_5$-C$_8$-cycloalkyl, which can be substituted by C$_1$-C$_5$-alkyl groups, hydroxy or alkali metal sulfonato groups, but does not denote unsubstituted C$_1$-C$_4$-alkyl if R$^{1a}$(CH$_2$)$_{m^a}$C(O)CR$^{3a}$C(O)R$^{2a}$ denotes 2,4-pentanedionato, 1-phenyl-1,3-butanedionato or 1,3-diphenyl-1,3-propanedionato, and further does not denote unsubstituted alkyl when M$^a$ is titanium, X$^a$ denotes fluorine, chlorine or bromine, m$^a$ denotes the number 0 or 1, but does not denote 0 if R$^{1a}$ denotes hydrogen, and n$^a$ denotes the number 0 or 1, and, if R$^{4a}$ contains an amino group, hydrohalides thereof, are new and are thus a further subject of the invention.

Compounds of the general formula I$^{a'}$

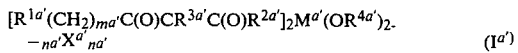

$$[R^{1a'}(CH_2)_{m^{a'}}C(O)CR^{3a'}C(O)R^{2a'}]_2 M^{a'}(OR^{4a'})_{2-n^{a'}}X^{a'}_{n^{a'}} \qquad (I^{a'})$$

wherein

M$^{a'}$ denotes titanium, zirconium or hafnium,

R$^{1a'}$ denotes hydrogen, C$_1$-C$_4$-alkyl or phenyl, which can be substituted by C$_1$-C$_2$-alkoxy, R$^{2a'}$ denotes methyl or phenyl, R$^{3a'}$ denotes hydrogen or phenyl, R$^{4a'}$ denotes C$_2$-C$_{16}$-alkyl, which can be substituted by hydroxyl, di-C$_1$-C$_3$-alkylamino or an alkali metal sulfonato group, or denotes 1-iso-propyl-4-methylcyclohex-2-yl, but does not denote unsubstituted C$_2$-C$_4$-alkyl, if R$^{1a'}$(CH$_2$)$_{m^{a'}}$C(O)CR$^{3a'}$-C(O)R$^{2a''}$ denotes 2,4-pentanedionate, 1-phenyl-1,3-butanedionato or 1,3-diphenyl-1,3-propanedionato, and further does not denote unsubstituted alkyl when M$^{a'}$ is titanium, X$^{a'}$ denotes chlorine, m$^{a'}$ denotes the number 1, if R$^{1a'}$ denotes hydrogen, or the number 0 or 1, if R$^{1a'}$ denotes phenyl, and n$^{a'}$ denotes the number 0 or 1, and, if R$^{4a'}$ contains an amino group, hydrochlorides thereof, are preferred.

Chloro-(2,3-dimethyl-2,3-butanediolato)-bis-(1-phenyl-1,3-butanedionato)-titanium(IV), chloro-(2-hydroxypropanolato)-bis-(1-phenyl-1,3-butanedionato)-titanium(IV), bis-(tridecanolato)-bis-(1-phenyl-1,3-butanedionato)-titanium(IV) and diethoxy-bis-(3-phenyl-2,4-pentanedionato)-titanium(IV) are particularly preferred.

By hydrohalides there are to be understood hydrochlorides, hydrobromides and hydroiodides, hydrochlorides being preferred.

By an alkali metal sulfonato group there is understood an A—SO$_3$ radical wherein A denotes an alkali metal. The sodium sulfonato radical is preferred.

By C$_1$-C$_{18}$-alkyl radicals there are to be understood branched and straight-chain alkyl radicals with one to eighteen carbon atoms. Alkyl radicals with more than ten carbon atoms are preferably straight-chain.

By C$_1$-C$_3$-alkylamines there are understood mono- and di-C$_1$-C$_3$-alkylamines, diethylamine being preferred.

By C$_5$-C$_8$-cycloalkyl there are to be understood cycloalkyl radicals with five to eight ring carbon atoms, cyclohexyl being preferred.

The metal complexes are prepared either by reacting the corresponding metal tetraalcoholate with the corresponding diketone in a molar ratio of 1:2 [A. Yamamoto, S. Kambara, J. Am. Chem. Soc. 79, 4,344 (1957)], or by reacting the corresponding dihalogenobis-(diketonato)-metal(IV) with the corresponding alcohol or its alcoholate, preferably the alkali metal alcoholate, in a molar ratio of 1:1, if a monohalogenometal(IV) complex (n in the general formula I denotes 1) is to be prepared, or in a molar ratio of 1:2, if a dialcoholatobis-diketonatometal(IV) complex (n is the general formula I denotes 0) is to be prepared [D. M. Puri, R. C. Mehrotra, J. Ind. Chem. Soc. 39, 499 (1962)]. It is advantageous to carry out the reaction of a dihalogenobis-(diketonato)metal(IV) complex with an alcohol in the presence of a base. Ammonia is advantageously used as the base, and is pased through the reaction mixture. The ammonium halide formed is only sparingly soluble in the solvents used, and can be separated off by filtration and/or centrifugation. Residues of the ammonium halide can be removed from the end product by sublimation under a high vacuum. The alcoholato groups of the alcoholato-diketonatometal(IV) complexes can be replaced by other alcoholato groups [U. B. Saxena et al., J. Chem. Soc. A 1970, 904; D. M. Puri, R. C. Mehrotra, J. Indian Chem. Sos. 39, 499 (1962)]. The alcoholatodiketonatometal(IV) complex of which the alcoholate groups are to be replaced is heated, as such or in a suitable solvent, together with an alcohol, which is preferably used in excess. This method is suitable, above all, for replacing a lower alcoholate anion by the alcoholate anion of a higher alcohol. In many cases, the replacement can be promoted by azeotropic distillation of the alcohol released. The reactions are advantageously carried out under a dry, inert gas atmosphere, preferably a nitrogen atmosphere, using anhydrous starting materials and, if necessary, carefully dried solvents.

The reactions are carried out either without a solvent or in inert solvents, such as, for example, benzene, n-hexane, diethyl ether, methylene chloride or chloroform. In particular, the reaction can be carried out without a solvent if at least one of the reactants is in the form of a liquid. If one of the reactants is insoluble in the solvent used, it is taken as a suspension in this solvent, and the soluble reactant is added dropwise as a solution.

The reaction is carried out at room temperature, with cooling or with heating, for example under reflux, depending on how vigorous it is. In order to bring the reaction to completion, it may be necessary to heat the reaction mixture under reflux for one to three days. In the case of reaction in which hydrogen halide is liberated, it is advantageous to expel this gas by passing dry nitrogen through the reaction mixture. The reaction products are precipitated from the reaction solution either by concentration and/or cooling and/or by addition of precipitating solvents, in particular hexane or petroleum ether.

The 1,3-diketones are known, or they can be prepared by methods which are known per se. For example, they can be obtained by ester condensation of the corresponding aryl methyl ketone with ethyl acetate, or of the corresponding ethyl aryl acetate with sodium amide, as the condensing agent (J. T. Adams, C. R. Hauser, J. Amer. Chem. Soc. 66, 1,220 [1944]). It is also possible to obtain the 1,3-diketones by addition of the corresponding aryl methyl ketone, dissolved in ethyl acetate, to a suspension of sodium in benzene or toluene (D. W. Brown, S. F. Dyke, M. Sainsbury, G. Hardy, J. Chem. Soc. (c) 1971, 3,219). A further possibility consists in reacting aryl methyl ketones with acetic anhydride in the presence of boron trifluoride [H. G. Walker, C. R. Hauser, J. Amer. Chem. Soc. 68, 2,742 (1946)]. 1-Benzyl-1,3-diketones are prepared by condensation of the corresponding ethyl phenyl acetate with the corresponding methyl ketone in the presence of sodium amide [A. Becker, Helv. Chim. Acta 149, 1,114 (1949)].

The invention furthermore relates to a process for the preparation of the compounds of the general formulae $I^a$ and $I^{a'}$, wherein $M^a$ and $M^{a'}$, $R^{1a}$ and $R^{1a'}$, $R^{2a}$ and $R^{2a'}$, $R^{3a}$ and $R^{3a'}$, $R^{4a}$ and $R^{4a'}$, $X^a$ and $X^{a'}$, $m^a$ and $m^{a'}$ and $n^a$ and $n^{a'}$ have the abovementioned meanings, 50 which is characterized in that (a) a tetraalkoxymetal(IV) compound $M^a(OR^{4a})_4$ or $M^{a'}(OR^{4a'})_4$, wherein $M^a$ and $M^{a'}$ and $R^{4a}$ and $R^{4a'}$ have the abovementioned meanings, is reacted with a diketone $R^{1a}(CH_2)_{m^a}C(O)CHR^{3a}C(O)R^{2a}$ or $R^{1a'}(CH_2)_{m^{a'}}C(O)CHR^{3a'}C(O)R^{2a'}$, wherein $R^{1a}$ and $R^{1a'}$, $R^{2a}$ and $R^{2a'}$, $R^{3a}$ and $R^{3a'}$ and $m^a$ and $m^{a'}$ have the abovementioned meanings, in an inert solvent with exclusion of moisture, or (b) a dihalogenobis-(diketonato)-metal(IV) compound $[R^{1a}(CH_2)_{m^a}C(O)CR^{3a}C(O)R^{2a}]_2M^aX^a_2$ or $[R^{1a'}(CH_2)_{m^{a'}}C(O)CR^{3a'}C(O)R^{2a'}]_2M^{a'}X^{a'}_2$, wherein $M^a$ and $M^{a'}$, $R^{1a}$ and $R^{1a'}$, $R^{2a}$ and $R^{2a'}$, $R^{3a}$ and $R^{3a'}$, $X^a$ and $X^{a'}$ and $m^a$ and $m^{a'}$ have the abovementioned meanings, is reacted with an alcohol $HOR^{4a}$ or $HOR^{4a'}$ or the corresponding alkali metal alcoholate, wherein $R^{4a}$ and $R^{4a'}$ have the abovementioned meanings, or (c) a compound of the general formula $I^a$ or $I^{a'}$, wherein $n^a$ and $n^{a'}$ denote O and $M^a$ and $M^{a'}$, $R^{1a}$ and $R^{1a'}$, $R^{2a}$ and $R^{2a'}$, $R^{3a}$ and $R^{3a'}$, $R^{4a}$ and $R^{4a'}$ and $m^a$ and $m^{a'}$ have the abovementioned meanings, is reacted with an alcohol $HOR^{4a}$ or $HOR^{4a'}$, wherein $R^{4a}$ and $R^{4a'}$ have the abovementioned meanings.

The medicaments according to the invention are above all administered intravenously, but also intramuscularly, intraperitoneally, subcutaneously, rectally or perorally. External application is also possible. Administration by intravenous injection or intravenous infusion is preferred.

The medicaments are produced by processes which are known per se, the complex compounds being employed as such or, if appropriate, in combination with suitable pharmaceutical excipients. If the new pharmaceutical formulations contain pharmaceutical excipients in addition to the active compound, the content of active compound in these mixtures is 0.1 to 99.5, preferably 0.5 to 95, percent by weight of the total mixture.

In accordance with the invention, the active compounds can be used in any suitable form, provided that the establishment and maintenance of sufficient levels of active compound are ensured. This can be achieved, for example, by oral or parenteral administration in suitable doses. The pharmaceutical formulation of the active compounds is expediently in the form of unit doses appropriate for the desired administration. A unit dose can be, for example, a dragee, a capsule, a suppository or a measured volume of a powder, of a granular material, of a solution, of an emulsion or of a suspension.

"Unit dose" for the purpose of the present invention means a physically discrete unit which contains an individual amount of the active ingredient in combination with a pharmaceutical excipient, the content of active compound in the unit dose corresponding to a fraction or a multiple of a therapeutic individual dose. An individual dose preferably contains the amount of active compound which is given in one administration and usually corresponds to a whole daily dose or a half, one-third or one-quarter of the daily dose. If only a fraction, such as a half or one-quarter, of the unit dose is required for an individual therapeutic administration, the unit dose is advantageously divisible, for example in the form of a tablet with a breaking groove.

When in the form of unit doses and intended, for example, for administration to humans, the pharmaceutical formulations according to the invention can contain about 0.1 to 500 mg, advantageously 10 to 200 mg and in particular 50 to 150 mg, of active compound.

In general, it has proved advantageous in human medicine to administer the active compound or compounds, when these are given parenterally, in a daily dose of about 0.1 to about 5, preferably 1 to 3, mg/kg of body weight, if appropriate in the form of several, preferably 1 to 3, individual administrations, to achieve the desired results. An individual administration contains the active compound or compounds in amounts of about 0.1 to about 5, preferably 1 to 3, mg/kg of body weight. Similar dosages can be used for oral treatment.

The pharmaceutical formulation can be administered, for therapeutic purposes, 1 to 4 times daily at fixed or varying points in time, for example after each meal and/or in the evening. However, it may be necessary to deviate from the dosages mentioned, and in particular to do so in accordance with the nature, body weight and age of the patient to be treated, the nature and severity of the disease, the nature of the formulation and of the administration of the medicament, and the time or interval over which administration takes place. Thus, in some cases it may be sufficient to manage with less than the abovementioned amount of active compound, whilst in other cases the abovementioned amount of active compound must be exceeded. As is customary in internal tumor therapy, treatment with the medicaments according to the invention can be combined with administration of other cytostatic agents having different action spectra, in order to reduce the risk of side-effects. It may also be appropriate to carry out treatment in accordance with the principle of cyclic cytostatic therapy. In this therapy, each treatment is followed by a recovery phase. The experience that, in most organs, healthy tissue regenerates more rapidly than malignant tissue is utilized therein.

The optimum dosage and mode of administration of the active compounds required in each particular case can easily be determined by any expert on the basis of his expert knowledge.

The pharmaceutical formulations as a rule consist of the complexes and non-toxic, pharmaceutically acceptable medicinal excipients, which are used in an admixture or diluent in solid, semi-solid or liquid form, or as a means of encasing, for example in the form of a capsule, a tablet coating, a sachet or some other container, for the therapeutically active ingredient. An excipient can, for example, serve as a promoter of the absorption of the medicament by the body, as a formulating auxiliary, as a sweetener, as a flavor correctant, as a colorant or as a preservative.

Examples of forms which may be used orally are tablets, dragees, hard and soft capsules, for example made of gelatin, dispersible powders, granules, aqueous and oily suspensions, emulsions, solutions or syrups.

Tablets may contain inert diluents, for example calcium carbonate, calcium phosphate, sodium phosphate or lactose; granulating agents and dispersing agents, for example maize starch or alginates; binders, for example starch, gelatin or gum acacia; and lubricants, for example aluminum stearate or magnesium stearate, talc or silicone oil. The tablets may additionally be provided with a coating, which can also be such that delayed dissolution and absorption of the medicament in the gastrointestinal tract and hence, for example, better tolerance, a protracted effect or a retarded effect are achieved. Gelatin capsules may contain the medicament mixed with a solid diluent, for example calcium carbonate or kaolin, or an oily diluent, for example olive oil, groundnut oil or paraffin oil.

Aqueous suspensions may contain suspending agents, for example sodium carboxymethylcellulose, methylcellulose, hydroxypropylcellulose, sodium alginate, polyvinylpyrrolidone, gum tragacanth or gum acacia; dispersing agents and wetting agents, for example polyoxyethylene stearate, heptadecaethyleneoxycetanol, polyoxyethylene sorbitan fatty acid esters, such as, for example, polyoxyethylene sorbitan monooleate, or lecithin; preservatives, for example methyl or propyl hydroxybenzoate; flavoring agents; and sweeteners, for example sucrose, lactose, sodium cyclamate, dextrose or invert sugar syrup.

Oily suspensions may contain, for example, groundnut oil, olive oil, sesame oil, coconut oil or paraffin oil, and thickeners, such as, for example, beeswax, hard paraffin or cetyl alcohol; and furthermore sweeteners, flavoring agents and antioxidants.

Water-dispersible powders and granules may contain the complexes mixed with dispersing agents, wetting agents and suspending agents, for example those mentioned above, as well as with sweeteners, flavoring agents and colorants.

Emulsions may contain, for example, olive oil, groundnut oil or paraffin oil, in addition to emulsifying agents, such as, for example, gum acacia, gum tragacanth, phosphatides, sorbitan monooleate or polyoxyethylene sorbitan monooleate, and sweeteners and flavoring agents.

For parenteral administration of the medicaments, sterile injectable aqueous suspensions, isotonic salt solutions or other solutions which contain dispersing agents or wetting agents and/or pharmacologically acceptable diluents, for example propylene glycol or butylene glycol, and/or solubilizing agents, for example Tweens ®, Cremophors ® or polyvinylpyrrolidone, are used.

It is particularly advantageous to mix solutions of the complexes in an anhydrous organic solvent with solutions of hydrophilic polymers, such as, for example, polyvinylpyrrolidones (PVP) or polyoxyethylene sorbitan fatty acid esters (Tween ®) or, in particular, glycerolpolyethylene glycol ricinoleate (Cremophor ®EL), and, after stripping off the solvent or solvents, to administer the remaining residues in the form of sterile aqueous solutions. Organic solvents which can be used, for example, are chloroform and methylene chloride, which are rendered anhydrous in the customary manner before being used. It has proved advantageous to use the hydrophilic polymers in a 5- to 50-fold, preferably 10- to 35-fold, excess by weight with respect to the complexes. It is also possible to introduce the polymers as such into solutions of the complexes. The residue which remains after stripping off the solvent or solvents is expediently freed as far as possible from solvent residues under a high vacuum. Solid crystalline or vitreous residues, or liquid or tacky residues are obtained, depending on the nature and amount of the hydrophilic polymer used. The latter residues can as a rule be converted into solid, in most cases waxy products by cooling. In the context of the present invention, these residues may be called coprecipitates. Addition also of a dispersing agent or wetting agent, such as propylene glycol or butylene glycol, preferably propylene glycol, to the mixture of the solutions of the complex compound and of the hydrophilic polymer during the preparation of the coprecipitates has an advantageous effect on the dissolving properties of the latter.

Aqueous solutions of the coprecipitates are prepared by treating the coprecipitates with water. As a rule, PVP-coprecipitates already dissolve at room temperature. Coprecipitates with polyoxyethylene sorbitan fatty acid esters or glycerol-polyethylene glycol ricinoleate are advantageously dissolved by warming the coprecipitate and the water to 25° to 60° C., preferably 30° to 40° C., before they are brought together.

It is particularly advantageous to dissolve the coprecipitates in physiological saline solution instead of in water.

The present invention also preferably relates to coprecipitates obtained from the complex compounds of the general formula I given above, wherein M, $R^1$, $R^2$, $R^3$, $R^4$, X, m and n have the meanings given above, and hydrophilic polymers, processes for the preparation of these coprecipitates, and aqueous solutions containing these coprecipitates.

The active compound can also be in a microencapsulated form, if appropriate together with one or more of the abovementioned excipients or additives.

PREPARATION EXAMPLES

1. Diethoxybis-(1-phenyl-1,3-butanedionato)-titanium-(IV)

15.8 g (0.097 mole) of benzoylacetone in 200 ml of dry n-hexane are rapidly added dropwise to 11.4 g (0.05 mole) of titanium tetraethoxide, with exclusion of moisture. The reaction mixture is heated under reflux in a dry nitrogen atmosphere for two hours. The colorless product which precipitates is filtered off with suction, suspended in boiling hexane, filtered off with suction again and freed from solvent residues under a high vacuum.

Melting point: 110° C.

A further preparation method can be found in O. M. Puri, R. C. Mehrotra, J. Ind. Chem. Soc. 39 (8), 499 (1962).

2. Diethoxybis-(1-phenyl-2,4-pentanedionato)-titanium-(IV)

2.2 ml (0.0105 mole) of titanium tetraethoxide are added to 3.7 g (0.021 mole) of 1-phenyl-2,4-pentanedione in a dry nitrogen atmosphere, with vigorous stirring. The volatile constituents are stripped off from the yellow reaction mixture, first under a water-pump vacuum and then under an oilpump vacuum. 5.1 g of a red oil remain.

Yield: quantitative.

Analysis: calculated: 63.93% C; 6.60% H; 9.81% Ti; found: 63.44% C; 6.71% H; 10.14% Ti.

1-Phenyl-2,4-pentanedione is prepared in accordance with the method of R. Levine et al., J. Am. Chem. Soc. 67, 1,510 (1945).

3. Diethoxybis-(4,4-dimethyl-1-phenyl-1,3-entanedionato)-titanium(IV)

5.28 g (0.0097 mole) of the title compound are obtained as a reddish-yellow oil in quantitative yield from 3.95 g (0.0194 mole) of 4,4-dimethyl-1-phenyl-1,3-pentanedione and 2.21 g (0.0097 mole) of titanium tetraethoxide by a procedure analogous to that in Example 2.

Analysis: calculated: 66.17% C; 7.40% H; 8.80% Ti; found: 66.44% C; 7.57% H; 8.34% Ti.

The preparation of 4,4-dimethyl-1-phenyl-1,3-pentanedione is described by R. Levine et al.; J. Am. Chem. Soc. 73, 5.614 (1951).

4. Diethoxybis-(1-phenyl-1,3-hexanedionato)-titanium-(IV)

5 g (0.0097 mole) of the title compound are obtained as a yellow oil in quantitative yield from 3.69 g (0.0194 mole) of 1-phenyl-1,3-hexanedione and 2.21 g (0.0097 mole) of titanium tetraethoxide by a procedure analogous to that in Example 2.

Analysis: Calculated: 65.12% C; 7.02% H; 9.27% Ti; found: 65.38% C; 7.30% H; 9.30% Ti.

5. Diethoxybis-(1-phenyl-1,3-pentanedionato)-titanium-(IV)

4.73 g (0.0097 mole) of the title compound are obtained as a yellow oil in quantitative yield from 3.42 g (0.00194 mole) of 1-phenyl-1,3-pentanedione and 2.21 g (0.0097 mole) of titanium tetraethoxide by a procedure analogous to that in Example 2.

Analysis: calculated: 63.94% C; 6.60% H; 9.80% Ti; found: 63.92% C; 6.61% H; 9.67% Ti.

6. Di-(n-propoxy)-bis-(1-phenyl-1,3-butanedionato)-titanium(IV)

8.11 g (0.05 mole) of benzoyl acetone in benzene are added to a solution of 7.1 g (0.025 mole) of titanium tetra-n-propoxide in benzene in a dry nitrogen atmosphere. After the mixture has been boiled under reflux for 3 hours, the benzene is distilled off, the residue is taken up in diethyl ether and the title compound is precipitated by addition of n-hexane and dried under a high vacuum.

Yield: 11.5 g (94% of theory); melting point: 133° C.

Analysis: calculated: 63.9% C; 6.6% H; 9.8% Ti; found: 63.5% C; 6.5% H; 10.3% Ti.

7. Bis-(sodium-2-sulfonatoethanolato)-bis-(1-phenyl-1,3-butanedionato)-titanium(IV)

2.96 g (0.022 mole) of the sodium salt of 2-hydroxyethanesulfonic acid are stirred under reflux with 4.41 g (0.01 mole) of dichloro-bis-(1-phenyl-1,3-butanedionato)-titanium(IV) in 250 ml of benzene in a dry nitrogen atmosphere for 3 days. When the evolution of hydrogen chloride has ended, a yellow product is precipitated from the yellow solution with petroleum ether (boiling point: 60° to 70° C.) and is dried under a high vacuum.

Yield: 6.4 g (96% of theory); melting point: 184° C.

Analysis: calculated: 43.4% C; 3.9% H; found: 43.4% C; 4.0% H.

8. Di-(2-propanolato)-bis-(1-phenyl-1,3-butanedionato)-titanium(IV)

4.05 g (0.025 mole) of benzoyl acetone in benzene are added to 3.55 g (0.0125 mole) of titanium tetraisopropoxide in benzene in a dry nitrogen atmosphere. The reaction mixture is heated under reflux for 2 to 3 hours and, after some of the benzene has been distilled off, hot n-hexane is added. The mixture is stirred during cooling, and the yellow product which has separated out is then filtered off with suction and dried under a high vacuum (literature: see Example 1).

Yield: 5.6 g (93% of theory); melting point: 89° C.

Analysis: calculated: 63.9% C; 6.6% H; 9.8% Ti; found: 63.9% C; 6.6% H; 9.6% Ti.

9. Chloro-(2-hydroxyethanolato)-bis-(1-phenyl-1,3-butanedionato)-titanium(IV)

0.62 g (0.01 mole) of ethylene glycol, dissolved in 40 ml of benzene, is added dropwise to 4.41 g (0.01 mole) of dichlorobis-(1-phenyl-1,3-butanedionato)-titanium-(IV) in 80 ml of benzene in a dry nitrogen atmosphere, with warming. When the evolution of hydrogen chloride has ended (after about three hours), the mixture is concentrated to dryness and the residue is taken up in methylene chloride. The yellow product is precipitated by addition of n-hexane and is dried under a high vacuum.

Yield: 4.25 g (91% of theory); melting point: 73° C.

Analysis: Calculated: 56.6% C; 5.0% H; 10.2% Ti; found: 57.1% C; 5.3% H; 10.8% Ti.

10. Chloro-(2-hydroxypropanolato)-bis-(1-phenyl-1,3-butanedionato)-titanium(IV)

0.76 g (0.01 mole) of 1,2-propanediol in 40 ml of benzene is added dropwise to 4.41 g (0.01 mole) of dichlorobis-(1-phenyl-1,3-butanedionato)-titanium(IV) in 80 ml of benzene in a dry nitrogen atmosphere, with warming. When the evolution of hydrogen chloride has ended, the yellow product is precipitated by addition of n-hexane. After being reprecipitated once from methylene chloride by means of n-hexane, the yellow powder is dried under a high vacuum.

Yield: 4.6 g (96% of theory); melting point: 78° C.

Analysis: calculated: 57.5% C; 5.2% H; 10.0% Ti; found: 57.5% C; 5.6% H; 10.6% Ti.

11. Tert.-butanolatochlorobis-(1-phenyl-1,3-butanedionato)-titanium(IV)

0.74 g (0.01 mole) of tert.-butanol, dissolved in 20 ml of methylene chloride, is added dropwise to 4.41 g (0.01 mole) of dichlorobis-(phenyl-1,3-butanedionato)-titanium(IV), suspended in 70 ml of methylene chloride, in a dry nitrogen atmosphere. The mixture is boiled under reflux until no further hydrogen chloride escapes. Petroleum ether (boiling point: 60° to 70° C.) is carefully added, until a brown oil separates out. When the oil has settled, the supernatant yellow solution is decanted and is concentrated until a yellow product precipitates. This is filtered off with suction and washed with a large quantity of petroleum ether.

Yield: 1.9 g (40% of theory); melting point: 70°–75° C.

Analysis: calculated: 60.2% C; 5.7% H; 10.0% Ti; found: 60.3% C; 5.9% H; 10.0% Ti.

12. Chloro-(2,3-dimethyl-2,3-butanediolato)-bis-(1-phenyl-1,3-butanedionato)-titanium(IV)

1.18 g (0.01 mole) of 2,3-dimethyl-2,3-butanediol, dissolved in 30 ml of methylene chloride, are added dropwise to a suspension of 4.41 g (0.01 mole) of dichlorobis-(1-phenyl-1,3-butanedionato)-titanium(IV) in 100 ml of dry methylene chloride in a dry nitrogen atmosphere. The mixture is boiled under reflux until no further hydrogen chloride escapes. Petroleum ether (boiling point: 60° to 79° C.) is added to the solution until it starts to become turbid. After the mixture has been left to stand at −18° C. for several hours, the yellow precipitate is filtered off and washed with petroleum ether.

Yield: 2.1 g (40% of theory); melting point: 80°–90° C.

Analysis: calculated: 59.7% C; 6.0% H; 9.2% Ti; found: 58.9% C; 6.3% H; 9.2% Ti.

13. Chloro-mentholato-bis-(1-phenyl-1,3-butanedionato)-titanium(IV)

1.56 g (0.01 mole) of methanol, dissolved in 30 ml of methylene chloride, are rapidly added dropwise to a suspension of 4.41 g (0.01 mole) of dichlorobis-(1-phenyl-1,3-butanedionato)-titanium(IV) in 70 ml of methylene chloride, in a dry nitrogen atmosphere. The mixture is boiled under reflux until evolution of hydrogen chloride has ended. After the mixture has been cooled to room temperature, the radiant yellow product is precipitated by careful addition of petroleum ether (boiling point: 60° to 70° C.). This product is filtered off with suction and washed with petroleum ether (boiling point: 60° to 70° C.).

Yield: 2.24 g (40% of theory); melting point: 95° C.

Analysis: calculated: 64.2% C; 6.7% H; 8.5% Ti; found: 64.2% C; 6.8% H; 8.6% Ti.

14. Diethoxybis-(1-phenyl-1,3-butanedionato)-hafnium(IV)

30.4 g of benzoyl acetone, dissolved in 200 ml of dry ether, are added dropwise to a suspension of 10 g of hafnium tetrachloride in 400 ml of dry ether under a stream of nitrogen and whilst boiling under reflux. After the mixture has been boiled under reflux for 24 hours, the precipitate formed is filtered off, washed twice with 100 ml portions of ether and dissolved in about 600 ml of chloroform. After the solution has been concentrated until turbidity appears, it is filtered and the solution is left to stand at −5° C. The colorless precipitate is recrystallized from chloroform. 6 g (33.7% of theory) of dichlorobis-(1-phenyl-1,3-butanedionato)-hafnium(IV) of melting point 231°–232° C. (red melt) are obtained.

5.71 g (0.01 mole) of dichlorobis-(1-phenyl-1,3-butanedionato)-hafnium(IV) and 1.2 g (0.026 mole) of absolute ethanol are stirred in 100 ml of benzene in a dry nitrogen atmosphere, whilst dry ammonia is passed in. When the exothermic reaction has subsided, the mixture is heated under reflux for four hours. Dry ammonia is then passed in at room temperature for three days. After the ammonium chloride formed has been centrifuged off, the solution is concentrated to dryness. The residue is dried under a high vacuum, white crystals subliming out at a bath temperature of 90° C. The title compound remains.

Yield: 4.41 g (74.7% of theory);

Melting point: 98° C. (agglomerates at 87°–97° C.).

Analysis: calculated: 48.78% C; 4.77% H; found: 50.09% C; 4.33% H.

15. Bis-(2-diethylaminoethoxy)-bis-(1-phenyl-1,3-butanedionato)-hafnium(IV) hydrochloride 5.71 g (0.01 mole) of dichlorobis-(1-phenyl-1,3-butanedionato)-hafnium(IV) and 2.34 g (0.02 mole) of freshly distilled diethylaminoethanol are stirred in 70 ml of dry methylene chloride in a firmly closed flask under a dry nitrogen atmosphere for two days. The reaction mixture is concentrated on a rotary evaporator and the residue is dried under a high vacuum.

Yield: 5.08 g (76% of theory);

Melting point: 135° C. (agglomerates from 125° C.).

16. Diethoxybis-(1-phenyl-1,3-butanedionato)-zirconium(IV)

Under a dry nitrogen atmosphere, 3.87 g (0.008 mole) of dichlorobis-(1-phenyl-1,3-butanedionato)-zirconium(IV) are suspended in 50 ml of dry methylene chloride, and a solution of 1.71 g (0.025 mole) of sodium ethanolate in 50 ml of absolute ethanol is added. After the mixture has been boiled under reflux for one day, dry ammonia is passed in for three days. After the precipitate has been filtered off, the filtrate is freed from residues of the precipitate by centrifugation. The clear solution is concentrated to dryness on a rotary evaporator and the residue is dried under a high vacuum, white crystals subliming out at a bath temperature of 90° C. The title compound remains.

Yield: 5.8 g (72% of theory);

Melting point: 122°–124° C.

17. Bis-(1-phenyl-1,3-butanedionato)-di-(n-propanolato)-zirconium(IV)

10.38 g (0.05 mole) of tetra-n-propoxyzirconium(IV) and 16.2 g (0.01 mole) of benzoyl acetone are dissolved in 100 ml of freshly distilled chlorobenzene. The chlorobenzene/propanol azeotrope is distilled off until a boiling point of 132° C. is reached. The mixture is then concentrated to dryness on a rotary evaporator. The residue is dried at 80° C. under a high vacuum for four hours and then overnight at room temperature.

Yield: 23.4 g (88% of theory);

Melting point: −6° C.

Analysis: calculated: 58.7% C; 6.1% H; found: 60.8% C; 5.5% H.

18. Di-(n-butanolato)-bis-(1-phenyl-1,3-butanedionato)-zirconium(IV)

28.62 g (0.0625 mole) of tetra-(n-butoxy)-zirconium(IV).butanol are reacted with 20.65 g (0.125 mole) of benzoyl acetone in 100 ml of chlorobenzene analogously to Example 17. The residue is dried at 70° C. under a high vacuum for five hours and then at room temperature for ten hours.

Yield: 28.7 g (82% of theory);
Melting point: −2° C.
Analysis: calculated: 60.1% C; 6.5% H; found: 58.3% C; 6.3% H.

19. Bis-(tridecanolato)-bis-(1-phenyl-1,3-butanedionato)-titanium(IV)

A solution of 4.0 g (0.02 mole) of 1-tridecanol (tridecyl alcohol, $CH_3(CH_2)_{12}OH$) in 50 ml of methylene chloride is rapidly added dropwise to a solution of 4.6 g (0.01 mole) of diethoxybis-(1-phenyl-1,3-butanedionato)-titanium(IV) in 100 ml of methylene chloride under a dry nitrogen atmosphere. The mixture is stirred at room temperature for 2 hours and is then concentrated on a rotary evaporator. The resulting red oil is freed from volatile substances under a high vacuum. It decomposes from 250° C.

Yield: 7.68 g (100% of theory); boiling point (26.6 Pa): 140° C.

Analysis: calculated: 70.2% C; 9.5% H; 6.1% Ti; found: 69.5% C; 9.4% H; 6.0% Ti.

20. Diethoxybis-[1-(3,4-dimethoxyphenyl)-1,3-butanedionato]-titanium(IV)

2.28 g (0.01 mole) of titanium tetraethoxide in 50 ml of methylene chloride are rapidly added dropwise to a solution of 4.44 g (0.02 mole) of 1-(3,4-dimethoxyphenyl)-1,3-butanedione in 20 ml of methylene chloride, in a dry nitrogen atmosphere. The clear yellow solution is stirred at room temperature for one and a half hours and then concentrated to dryness. The yellow residue is dried under a high vacuum.

Yield: quantitative; melting point: 98°–105° C.

Analysis: calculated: 57.9% C; 6.3% H; found: 58.2% C; 6.3% H.

21. Diethoxybis-(3-phenyl-2,4-pentanedionato)-titanium(IV)

2.3 g (0.01 mole) of tetraethoxytitanium(IV) and 3.5 g (0.02 mole) of 3-phenyl-2,4-pentanedione in 100 ml of benzene are boiled under reflux. The ethanol/benzene azeotrope is distilled off until a boiling point of 80° C. is reached. The reddish-brown clear solution is concentrated to dryness. The remaining reddish-yellow residue is recrystallized from benzene and dried under a high vacuum.

Yield: 3.2 g (65% of theory).
Melting point: 103°–112° C. (decomposition).
Analysis: calculated: 63.93% C; 6.60% H; 9.81% Ti; found: 63.78% C; 6.67% H; 9.72% Ti.

3-Phenyl-2,4-pentanedione was prepared as described by J. T. Adams and C. R. Hauser, *J.Am.Chem.Soc.* 67, 284(1945).

22. Coprecipitate of diethoxy-bis-(1-phenyl-1,3-butanedionato)-titanium(IV)/Cremophor®EL 1:10

Solutions of 1 g of diethoxy-bis-(1-phenyl-1,3-butanedionato)-titanium(IV) and 10 g of dried Cremophor-®EL (Messrs BASF) in dry pure ethanol are prepared in a dry nitrogen atmosphere. When the two solutions have been combined, the solvent is stripped off under reduced pressure. The yellowish coprecipitate which remains is then kept under a high vacuum for 24 hours. The coprecipiate is dissolved in water or physiological saline solution.

A solution of the coprecipitate in physiological saline solution is particularly advantageously prepared by injecting the coprecipitate, which has been prewarmed in a syringe to 40° C., into a physiological saline solution (0.9% strength aqueous sodium chloride solution), which has also been prewarmed to 40° C., with stirring.

PHARMACOLOGY

A. Tumor model

1. Sarcoma 180 tumor model (intraperitoneal)

In each case about $10^6$ sarcoma 180 tumor cells in 0.2 ml of physiological saline solution are transferred intraperitoneally (i.p.) to female NMRI mice which are about 6 weeks old and weigh 18 to 20 g. The tumor is kept in passage in the same mouse strain. The tumor cells are removed from freshly killed animals immediately before transplantation. On inoculation, the animals are randomized. 6 mice are used per dosage. The number of control groups (untreated animals) is chosen such that it corresponds to about the square root of the total number of groups. The substances are injected intraperitoneally, in each case 24 hours after the transplantation, as suspensions in customary solubilizing agents, such as, for example, Tween ®(polyoxyethylene derivatives of sorbitan esters).

2. Sarcoma 180 tumor model (subcutaneous)

In each case about $20 \times 10^6$ sarcoma 180 tumor cells in 0.2 ml of physiological saline solution are transferred subcutaneously (s.c.) to NMRI mice like those under 1. When the average tumor weight is 0.5 g, which under the given experimental conditions, is achieved after about 8 days, therapy is started. The metal complexes are administered twice weekly into the tail vein as solutions of coprecipitates in physiological saline solution.

Throughout the experiment, the tumor weight is estimated in the conventional manner by palpation and comparison with standardized kneaded balls.

3. Ehrlich ascites tumor model

In each case $10^6$ Ehrlich ascites tumor cells in 0.2 ml of physiological saline solution are transferred intraperitoneally on day 0 to NMRI mice like those under 1. On day 1, the metal complexes are administered intraperitoneally as solutions of coprecipitates in physiological saline solution. On day 10, the animals are sacrificed and the Ehrlich ascites tumor cells are counted. Three animals are used in each group. B. Experimental results The results from the sarcoma 180 tumor model described under point A 1. are summarized in Table I which follows. The stated dose was administered once at the start of the experiment, as described. The factor T/C given in percent denotes the percentage increase in median survival time of the treated animals compared with the median survival time of the untreated control animals.

The experiment is discontinued as soon as the median survival time T/C of the treated animals has reached 300% of the median survival time of the untreated animals. In calculating the median survival time, the animals still alive at the end of the experiment are taken as being dead at the end of the experiment. The comparison compound cisplatin has a therapeutic action in a dose range from about 8 to 10 mg/kg, and most of the animals are cured. At a dose of about 20 mg/kg, the median survival time of the animals treated with cisplatin is already shorter than that of the untreated control animals.

TABLE I

| $[R^1(CH_2)_mC(O)CR^3C(O)R^2]_2M(OR^4)_{2-n}X_n$ | | | | | | | | Dose [mg/kg] | T/C [%] |
|---|---|---|---|---|---|---|---|---|---|
| $R^1$ | $R^2$ | $R^3$ | $R^4$ | M | X | m | n | | |
|  | CH₃ | H | C₂H₅ | Ti | — | 0 | 0 | 18<br>92<br>198 | 300<br>279<br>300 |
|  | CH₃ | H | n-C₄H₉ | Ti | — | 0 | 0 | 222 | 139 |
|  | CH₃ | H | n-C₃H₇ | Ti | — | 0 | 0 | 210 | 133 |
|  | CH₃ | H | i-C₃H₇ | Ti | — | 0 | 0 | 20<br>98 | 283<br>195 |
|  | CH₃ | H | t-C₄H₉ | Ti | Cl | 0 | 1 | 96<br>206 | 184<br>204 |
|  | CH₃ | H | NaSO₃CH₂CH₂ | Ti | — | 0 | 0 | 133<br>286 | 144<br>224 |
|  | n-C₃H₇ | H | C₂H₅ | Ti | — | 0 | 0 | 222 | 153 |
|  | CH₃ | H | (CH₃)₂C(OH)C(CH₃)₂ | Ti | Cl | 0 | 1 | 21<br>105 | 242<br>138 |
|  | CH₃ | H | CH₃CH(OH)CH₂ | Ti | Cl | 0 | 1 | 19<br>94<br>203 | 215<br>283<br>283 |
|  | CH₃ | H | HOCH₂CH₂ | Ti | Cl | 0 | 1 | 19<br>93<br>201 | 145<br>283<br>211 |
|  | CH₃ | H | C₂H₅ | Ti | — | 1 | 0 | 98<br>210 | 144<br>195 |
| CH₃ | CH₃ |  | C₂H₅ | Ti | — | 0 | 0 | 20<br>98<br>210 | 300<br>250<br>214 |
|  |  | H | C₂H₅ | Ti | — | 0 | 0 | 251 | 300 |
|  | CH₃ | H | CH₃(CH₂)₃CH(C₂H₅)—CH₂ | Ti | — | 0 | 0 | 25<br>125<br>269 | 233<br>233<br>273 |
|  | CH₃ | H | 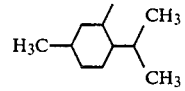 | Ti | Cl | 0 | 1 | 22<br>112<br>241 | 197<br>187<br>172 |
|  | CH₃ | H | CH₃(CH₂)₁₂ | Ti | — | 0 | 0 | 31<br>154 | 300<br>300 |
|  | C₂H₄ | H | C₂H₅ | Ti | — | 0 | 0 | 20<br>98<br>210 | 204<br>276<br>135 |
| t-C₄H₉ | CH₃ | H | C₂H₅ | Ti | — | 0 | 0 | 181 | 165 |

Table II which follows shows the results with the sarcoma 180 tumor model described under point A 2. It can be seen that there is a significant decrease in tumor weight in comparison with the control animals.

TABLE II

| Substance[1] | Number of animals | Dose [mg/kg] | Tumor weight [g] | | | | | | |
|---|---|---|---|---|---|---|---|---|---|
| | | | Day 0 | Day 8 | Day 13 | Day 16 | Day 20 | Day 23 | Day 27 |
| Control | 12+ | 0 | Tumor trans- planta- tion | 0.5 | 0.85 | 0.85 | 1.1 | 0.75 | 0.8 |
| Ti(bzac)$_2$(OEt)$_2$ | 6 | 5 | | 0.5 | 0.5 | 0.45 | 0.3 | 0.15 | 0 |
| T60 1:30 | 6 | 10 | | 0.65 | 0.5 | 0.6 | 0.55 | 0.35 | 0.5 |
| | 6 | 20 | | 0.5 | 0.4 | 0.35 | 0.25 | 0.15 | 0.05 |
| Ti(bzac)$_2$(OEt)$_2$ | 6 | 5 | | 0.65 | 1.0 | 0.8 | 0.85 | 1.05 | 0.75 |
| Cremophor ® | 6 | 10 | | 0.5 | 0.5 | 0.35 | 0.2 | 0.1 | 0 |
| 1:10 | 6 | 20 | | 0.5 | 0.7 | 0.4 | 0.4 | 0.1 | 0 |
| Ti(bzac)$_2$(OEt)$_2$ | 6 | 5 | | 0.6 | 0.85 | 0.45 | 0.75 | 1.5 | 0.6 |
| PVP 30 BT | 6 | 10 | | 0.55 | 0.5 | 0.25 | 0.15 | 0 | 0 |
| 1:10 | 6 | 20 | | 0.8 | 0.7 | 0.24 | 0.3 | 0.3 | 0.15 |

+ 30 animals from day 20, since prior thereto, 18 control animals were inadvertently not taken into consideration;
[1]Ti(bzac)$_2$(OEt)$_2$ = diethoxy-bis-(l-phenyl-1,3-butanedionato)-titanium(IV)
T60 = Tween ® 60;
PVP 30 BT = polyvinylpyrrolidone having an average molecular weight of 30,000.

Table III which follows shows the results with the Ehrlich ascites tumor model described under point A3. A significantly lower number of Ehrlich ascites tumor cells are observed in the treated animals than in the untreated control animals.

TABLE III

| [R$^1$(CH$_2$)$_m$C(O)CR$^3$C(O)R$^2$]$_2$M(OR$^4$)$_{2-n}$X$_n$ | | | | | | | | Dose | Ehrlich Ascites cells |
|---|---|---|---|---|---|---|---|---|---|
| R$^1$ | R$^2$ | R$^3$ | R$^4$ | M | X | m | n | [mg/kg] | on day 10 |
| 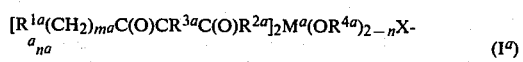 | CH$_3$ | H | C$_2$H$_5$ | Hf | — | 0 | 0 | 24 | 64.8 × 10$^7$ |
| | | | | | | | | 118 | 33.9 × 10$^7$ |
| | | | | | | | | 254 | 0 |
| 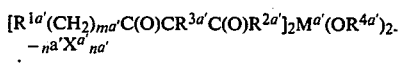 | CH$_3$ | H | HCl.(C$_2$H$_5$)$_2$NC$_2$H$_4$ | Hf | — | 0 | 0 | 347 | 0 |
| Control | | | | | | | | 0 | 102.5 × 10$^7$ |

What is claimed is:

1. A compound of the formula I$^a$ $$[R^{1a}(CH_2)_{ma}C(O)CR^{3a}C(O)R^{2a}]_2M^a(OR^{4a})_{2-n}X^a_{na} \quad (I^a)$$

wherein

M$^a$ denotes a member selected from the group consisting of titanium, zirconium and hafnium, R$^{1a}$ denotes hydrogen, C$_1$-C$_8$-alkyl, or phenyl, which is optionally monosubstituted or polysubstituted by fluorine, chlorine, bromine, nitro, C$_1$-C$_4$-alkyl, C$_1$-C$_4$-alkoxy or trifluoromethyl, R$^{2a}$ denotes C$_1$-C$_8$-alkyl, or phenyl, which is optionally monosubstituted or polysubstituted by fluorine, chlorine, bromine, nitro, C$_1$-C$_4$-alkyl, C$_1$-C$_4$-alkoxy or trifluoromethyl, R$^{3a}$ denotes hydrogen or phenyl, R$^{4a}$ denotes C$_1$-C$_{18}$-alkyl, which is optionally substituted by hydroxyl, C$_1$-C$_3$-alkylamino or alkalimetal sulfonato, or denotes C$_5$-C$_8$-cycloalkyl, which is optionally substituted by C$_1$-C$_5$-alkyl, hydroxy or alkali-metal sulfonato, but does not denote unsubstituted C$_1$-C$_4$-alkyl when R$^{1a}$(CH$_2$)$_{ma}$C(O)CR$^{3a}$C(O)R$^{2a}$ denotes 2,4-pentanedionato, 1-phenyl-1,3-butanedionato or 1,3-diphenyl-1,3-propanedionato and further does not denote unsubstituted alkyl when M$^a$ is titanium, X$^a$ denotes fluorine, chlorine or bromine, m$^a$ denotes the number 0 or 1, but does not denote 0 when R$^{1a}$ denotes hydrogen, and n$^a$ denotes the number 0 or 1, and, when R$^{4a}$ contains an amino group, a hydrohalide thereof.

2. A compound according to claim 1 of the formula I$^{a'}$ $$[R^{1a'}(CH_2)_{ma'}C(O)CR^{3a'}C(O)R^{2a'}]_2M^{a'}(OR^{4a'})_{2-na'}X^{a'}_{na'} \quad (I^{a'})$$

wherein

M$^{a'}$ denotes titanium, zirconium or hafnium,

R$^{1a'}$ denotes hydrogen, C$_1$-C$_4$-alkyl or phenyl, which is optionally substituted by C$_1$-C$_2$-alkoxy, R$^{2a'}$ denotes methyl or phenyl, R$^{3a'}$ denotes hydrogen or phenyl, R$^{4a'}$ denotes C$_2$-C$_{16}$-alkyl, which is optionally substituted by hydroxyl, di-C$_1$-C$_3$-alkylamino or an alkali-metal sulfonato group, or denotes 1-iso-propyl-4-methyl-cyclohex-2-yl, but does not denote unsubstituted C$_2$-C$_4$-alkyl when R$^{1a'}$(CH$_2$)$_{ma'}$C(O)CR$^{3a'}$C(O)R$^{2a''}$ denotes 2,4-pentanedionato, 1-phenyl-1,3-butanedionato or 1,3-diphenyl-1,3-propanedionato or when M$^a$ is titanium X$^{a'}$ denotes chlorine, m$^{a'}$ denotes the number 1, if R$^{1a'}$ denotes hydrogen, or the number 0 or 1, if R$^{1a'}$ denotes phenyl, and n$^{a'}$ denotes the number 0 or 1, and, when R$^{4a'}$ contains an amino group, a hydrochloride thereof.

3. The compound according to claim 2 which is chloro-(2,3-dimethyl-2,3-butanediolato)-bis-(1-phenyl-1,3-butanedionato)-titanium(IV).

4. The compound according to claim 2 which is chloro-(2-hydroxypropanolato)-bis-(1-phenyl-1,3-butanedionato)-titanium(IV).

5. A medicament composition comprising pharmaceutically-acceptable excipient and from 0.1 and 99.5 percent by weight of at least one metal complex of the general formula I, $$[R^1(CH_2)_mC(O)CR^3C(O)R^2]_2M(OR^4)_{2-n}X_n \quad (I),$$

wherein

M denotes titanium, zirconium or hafnium, $R^1$ denotes hydrogen, $C_1$–$C_8$-alkyl or phenyl, which is optionally monosubstituted or polysubstituted by fluorine, chlorine, bromine, nitro, $C_1$–$C_4$-alkyl, $C_1$–$C_4$-alkoxy or trifluoromethyl, $R^2$ denotes $C_1$–$C_8$-alkyl, or phenyl, which is optionally monosubstituted or polysubstituted by fluorine, chlorine, bromine, nitro, $C_1$–$C_4$-alkyl, $C_1$–$C_4$-alkoxy or trifluoromethyl, $R^3$ denotes hydrogen or phenyl, $R^4$ denotes $C_1$–$C_{18}$-alkyl, which is optionally substituted by hydroxyl, $C_1$–$C_3$-alkylamino or alkali-metal sulfonato, or denotes $C_5$–$C_8$-cycloalkyl, which is optionally substituted by $C_1$–$C_5$-alkyl, hydroxyl or alkali-metal sulfonato, X denotes fluorine, chlorine or bromine, m denotes the number 0 or 1, but does not denote 0 when $R^1$ denotes hydrogen, and n denotes the number 0 or 1, and, when $R^4$ contains an amino group, a hydrohalide thereof; the medicament composition comprising from 0.1 to 500 milligrams of metal complex per unit dose.

6. A medicament composition according to claim 5 comprising at least one metal complex of the formula I', $$[R^{1\prime}(CH_2)_{m'}C(O)CR^{3\prime}C(O)R^{2\prime}]_2M'(OR^{4\prime})_{2-n}X'_n \quad (I')$$

wherein

M' denotes titanium, zirconium or hafnium, $R^{1\prime}$ denotes hydrogen, $C_1$–$C_6$-alkyl, or phenyl, which can be monosubstituted or polysubstituted by fluorine, chlorine, bromine, nitro, $C_1$–$C_2$-alkyl, $C_1$–$C_2$-alkoxy or trifluoromethyl, $R^{2\prime}$ denotes $C_1$–$C_6$-alkyl or phenyl, which is optional substituted by $C_1$–$C_2$-alkoxy, $R^{3\prime}$ denotes hydrogen or phenyl, $R^{4\prime}$ denotes $C_2$–$C_{16}$-alkyl, which is optionally substituted by hydroxyl, $C_1$–$C_3$-alkylamino or alkali metal sulfonato, or denotes cyclohexyl, which is optionally substituted by $C_1$–$C_4$-alkyl, X' denotes fluorine or chlorine, m' denotes the number 0 or 1, but does not denote 0 if $R^{1\prime}$ denotes hydrogen, and n denotes the number 0 or 1, and, if $R^{4\prime}$ contains an amino group, a hydrohalide thereof.

7. A medicament composition according to claim 5, comprising at least one metal complex of the formula I'', $$[R^{1\prime\prime}(CH_2)_{m\prime\prime}C(O)CR^{3\prime\prime}C(O)R^{2\prime\prime}]_2M'\!-\!(OR^{4\prime\prime})_{2-n}X''_n \quad (I'')$$

wherein

M'' denotes titanium, zirconium or hafnium, $R^{1\prime\prime}$ denotes hydrogen, $C_1$–$C_4$-alkyl or phenyl, which is optional substituted by $C_1$–$C_2$-alkoxy, $R^{2\prime\prime}$ denotes $C_1$–$C_4$-alkyl or phenyl, $R^{3\prime\prime}$ denotes hydrogen or phenyl, $R^{4\prime\prime}$ denotes $C_2$–$C_{13}$-alkyl, which is optional substituted by a hydroxyl, a di-$C_1$–$C_3$-alkylamino or an alkali-metal sulfonato group, or denotes 1-isopropyl-4-methyl-cyclohex-2-yl, X'' denotes chlorine, m'' denotes the number 1 when $R^{1\prime\prime}$ denotes hydrogen, or the number 0 when $R^{1\prime\prime}$ denotes phenyl, and n denotes the number 0 or 1, and, when $R^{4\prime\prime}$ contains an amino radical, a hydrochloride thereof.

8. A medicament composition according to claim 5 comprising diethoxybis-(1-phenyl-1,3-butanedionato)-titanium(IV).

9. A medicament composition comprising pharmaceutically-acceptable excipient and from 0.1 to 99.5 percent by weight of a compound according to one of claims 2 to 4 and 1.

10. A pharmacologically-acceptable coprecipitate of at least one metal complex of the formula I $$[R^1(CH_2)_mC(O)CR^3C(O)R^2]_2M(OR^4)_{2-n}X_n \quad (I)$$

wherein

M denotes titanium, zirconium or hafnium, $R^1$ denotes hydrogen, $C_1$–$C_8$-alkyl or phenyl, which can be monosubstituted or polysubstituted by fluorine, chlorine, bromine, nitro, $C_1$–$C_4$-alkyl, $C_1$–$C_4$-alkoxy or trifluoromethyl, $R^2$ denotes $C_1$–$C_8$-alkyl, or phenyl, which is optionally monosubstituted or polysubstituted by fluorine, chlorine, bromine, nitro, $C_1$–$C_4$-alkyl, $C_1$–$C_4$-alkoxy or trifluoromethyl, $R^3$ denotes hydrogen or phenyl, $R^4$ denotes $C_1$–$C_{18}$-alkyl, which is optionally substituted by hydroxyl, $C_1$–$C_3$-alkylamino or alkali-metal sulfonato, or denotes $C_5$–$C_8$-cycloalkyl, which is optionally substituted by $C_1$–$C_5$-alkyl, hydroxyl or alkali-metal sulfonato, X denotes fluorine, chlorine or bromine, m denotes the number 0 or 1, but does not denote 0 when $R^1$ denotes hydrogen, and n denotes the number 0 or 1, and, when $R^4$ contains an amino group, a hydrohalide thereof, and a hydrophilic polymer.

11. A coprecipitate according to claim 10 wherein the hydrophilic polymer is polyvinylpyrrolidone.

12. A coprecipitate according to claim 10 wherein the hydrophilic polymer is a polyoxyethylene sorbitan fatty acid monoester.

13. A coprecipitate according to claim 10, characterized in that the hydrophilic polymer is glycerolpolyethylene glycol ricinoleate.

14. A coprecipitate according to claim 13 wherein the metal complex is diethoxybis-(1-phenyl-1,3-butanedionato)-titanium(IV).

15. A process for preparing a coprecipitate according to claim 14 which comprises concentrating to dryness a solution of the metal complex and of a pharmacologically-acceptable hydrophilic polymer in an inert organic solvent.

16. A process according to claim 15, characterized in that propylene glycol or butylene glycol is added to the solution of the metal complex and the hydrophilic polymer before concentration.

17. A sterile aqueous solution comprising a coprecipitate according to one of claims 10 to 13 and 14.

18. A medicament composition comprising pharmaceutically-acceptable excipient and from 0.1 to 99.5 percent by weight of at least one metal complex which is a compound according to claim 1.

19. A pharmacologically-acceptable coprecipitate of a hydrophilic polymer and at least one metal complex which is a compound according to claim 1.

20. A medicament composition comprising pharmaceutically-acceptable excipient and at least 0.1 percent by weight of at least one metal complex in the form of coprecipitate according to claim 10, the medicament composition comprising from 0.1 to 500 milligrams of metal complex per unit dose.

* * * * *